United States Patent [19]
Davis

[11] Patent Number: 5,190,548
[45] Date of Patent: Mar. 2, 1993

[54] SURGICAL REAMER

[75] Inventor: Robert Davis, Safety Harbor, Fla.

[73] Assignee: Linvatec Corporation, Largo, Fla.

[21] Appl. No.: 683,064

[22] Filed: Apr. 10, 1991

[51] Int. Cl.⁵ .............................................. A61F 5/04
[52] U.S. Cl. ...................... 606/80; 606/79; 408/209
[58] Field of Search ............ 606/53, 79, 80, 81, 606/86, 88, 96, 167, 170, 180; 408/203.5, 204, 224, 227, 229

[56] References Cited

U.S. PATENT DOCUMENTS

| | | | |
|---|---|---|---|
| 749,624 | 1/1904 | McCullough | 606/180 X |
| 930,477 | 8/1909 | Hudson | 606/170 X |
| 1,721,378 | 7/1929 | Draeger | 408/203.5 |
| 2,359,091 | 9/1944 | Eakin | 408/204 |
| 2,725,768 | 12/1955 | Jacot | 408/229 X |
| 2,847,885 | 8/1958 | Wagner | 408/204 X |
| 3,337,936 | 8/1967 | Curry | 408/227 |
| 3,554,192 | 1/1971 | Isberner | 606/79 X |
| 3,783,860 | 1/1974 | Burstein et al. | 606/79 X |
| 4,341,206 | 7/1982 | Perrett et al. | |
| 4,806,050 | 2/1989 | Bryant | 408/203.5 |

FOREIGN PATENT DOCUMENTS 0440371 1/1991 European Pat. Off. .
3800482 1/1988 Fed. Rep. of Germany .
7819240 6/1978 France .

OTHER PUBLICATIONS

Acufex Endoscopic Drill Guide system, Acufex Microsurgical, 1989.

*Primary Examiner*—Robert A. Hafer
*Assistant Examiner*—Sam Rimell

[57] ABSTRACT

A surgical bone reamer includes a rotatable, elongated shank having a proximal end, a distal end and a longitudinal axis, and a reaming head mounted on the distal end. A plurality of equally spaced walls are radially disposed on the reaming head around the longitudinal axis, and tip edges for penetrating bone are defined on the radial walls to be disposed angularly with the longitudinal axis. Reaming edges joined to the tip edges extend longitudinally from the tip edges in the proximal direction parallel to and an equal radial distance from the longitudinal axis for reaming a cylindrical tunnel when the reaming head is rotated in bone. Tapered flutes disposed angularly between the tip edges and the radial walls permit bone to be evacuated through the reaming head when forming a tunnel in bone.

32 Claims, 1 Drawing Sheet

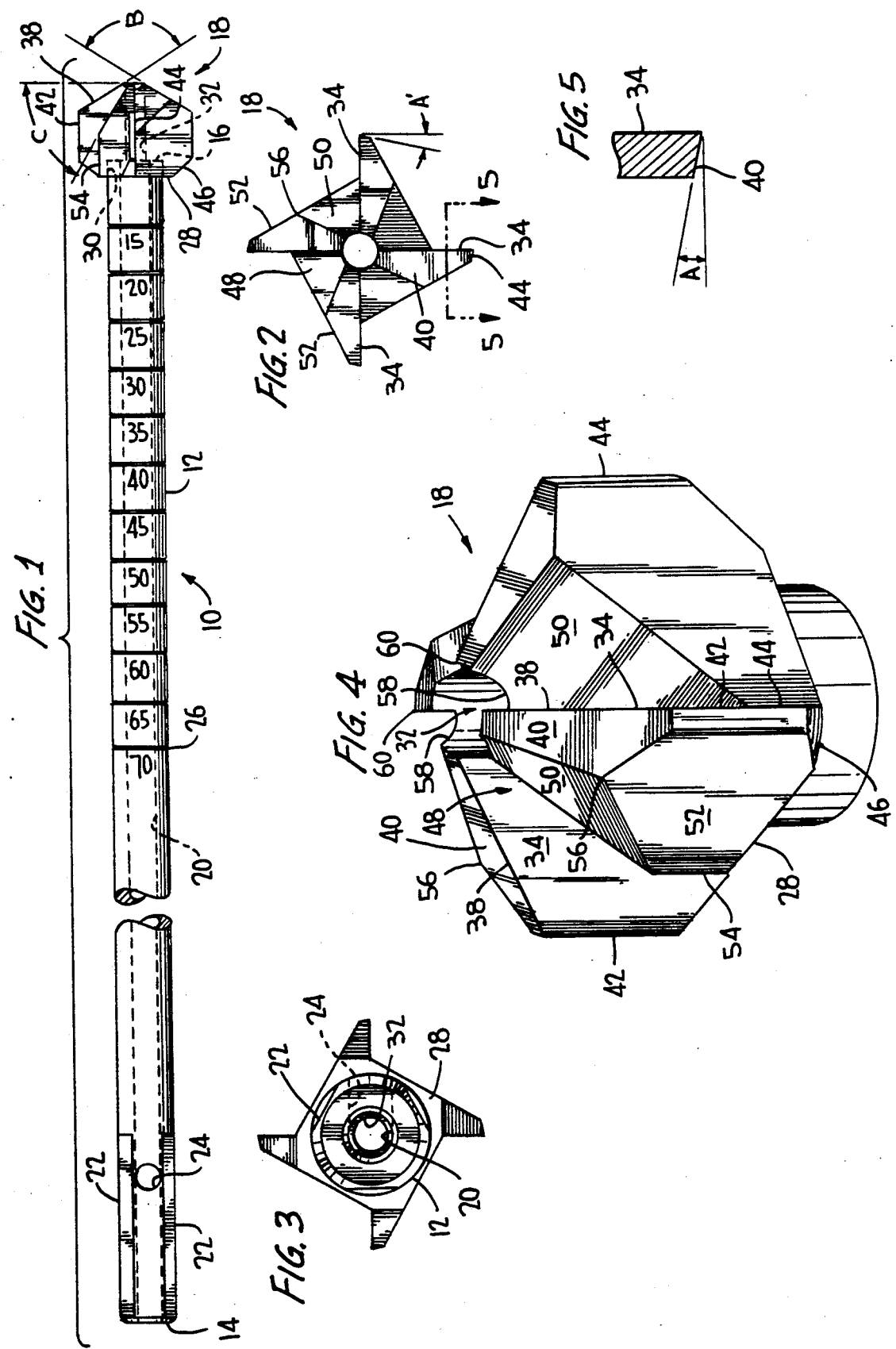

SURGICAL REAMER

BACKGROUND OF THE INVENTION

1. Field of the Invention

The present invention pertains to surgical instruments for forming a passage in bone and, more specifically, to a surgical reamer for forming straight, cylindrical tunnels in bone.

2. Description Of The Prior Art

Various surgical procedures, such as anterior and posterior cruciate ligament repair and reconstruction of the knee, involve forming a cylindrical passage or tunnel in bone. In anterior cruciate ligament reconstruction, for example, isometrically situated bone tunnels are drilled in the tibia and femur to receive the ends of a graft or prosthetic ligament positioned in the tunnels to extend intraarticularly across the knee joint. A fixation device, such as an interference bone screw, is inserted into the bone tunnels to engage the wall of the bone tunnels and bone blocks on the ends of the ligament and thereby fixate the ligament in bone. Although such procedures can be performed utilizing open surgical techniques, closed, or endoscopic, surgical techniques possess numerous benefits over open surgery. For instance, the benefits obtained with endoscopic anterior cruciate ligament repair and reconstruction include eliminating the need for an antero-medial arthrotomy, avoiding desiccation of articular cartilage, reducing post-surgical morbidity and pain, shortening hospitalization, permitting early range of motion and accelerating rehabilitation. When forming the tibial and femoral bone tunnels endoscopically, a surgical bone drill is typically inserted on a guide wire through a portal leading to the tibia to drill an open ended, cylindrical tunnel therein. The drill is then guided through the tibial tunnel across the knee joint to the femur, and a closed end, cylindrical tunnel is drilled in the femur. Proper fixation of the ligament in the bone tunnels in both open and closed surgical procedures requires accurate fit between the bone blocks, the fixation devices and the wall of the bone tunnels. Therefore, the bone tunnels must be correctly sized, substantially uniform in cross-section and longitudinally straight. However, presently available surgical drills for forming bone tunnels generate numerous inaccuracies in the bone tunnels that can impair ligament fixation and are generally incompatible with endoscopic procedures.

Surgical drills for forming tunnels in bone typically utilize drill bits having an angular drill tip joined to longitudinally tapered helical cutting edges separated by helical flutes. The longitudinal taper on such drill bits promotes deviation of the drill bits from a straight, longitudinal path during tunnel formation. Therefore, bone tunnels produced with such drills can be curved or irregular, and the cross-section of the bone tunnels can vary over the length of the bone tunnels. Inaccuracies in the longitudinal straightness and cross-sectional uniformity of the bone tunnels can inhibit graft entry and positioning in the bone tunnels, deter insertion of the fixation devices, cause divergence of the fixation devices reducing contact between the fixation devices, the bone blocks and the bone, cause convergence of the fixation devices with resultant crushing or fracturing of the ligament, and cause dislocation of the bone blocks when the fixation devices are inserted thereby compromising proper fixation and isometric positioning of the ligament. Moreover, the helical flutes on such drills tend to become impacted with bone when drilling a bone tunnel, and the drills must be withdrawn from the surgical site to remove the impacted material from the flutes. Withdrawal and reinsertion of the surgical drill increases the complexity and duration of the surgical procedure, particularly for closed, or endoscopic, surgery. A further drawback of prior art surgical drills is that bone fragments are not evacuated from the bone tunnels during the drilling process and are usually deposited within and on the walls of the bone tunnels. Accordingly, additional procedures must be implemented to clean out the bone tunnels and remove the fragments, and such procedures further complicate and protract the surgical procedure. Furthermore, surgical drill bits are commonly subject to drag forces when rotated in bone that inhibit forward advancement of the drill bits reducing drilling efficiency and increasing drilling time.

Surgical reamers for enlarging and shaping pre-drilled bone tunnels typically share the deficiencies noted above. Moreover, surgical reamers generally do not have angular tips enabling initial penetration and forward advancement through bone. Such reamers are ineffective in forming bone tunnels and produce bone smoke and heat related, bone necrosis. Furthermore, the bits on prior art surgical drills and reamers are relatively long and, when utilized in endoscopic anterior cruciate ligament repair and reconstruction, remain exposed at the knee joint during initial formation of the femoral bone tunnel. The bits remain exposed at the knee joint until the length of the femoral bone tunnel matches the length of the bits, and the duration of this exposure can be substantial when the bits are long. Exposure of the rotating bits at the knee joint presents a risk of damage to surrounding tissue, and this risk is significant with prolonged presence of the bits at the joint.

SUMMARY OF THE INVENTION

Accordingly, it is an object of the present invention to overcome the above disadvantages of prior art surgical bone drills and reamers.

It is also an object of the present invention to provide a surgical bone reamer for forming a longitudinally straight bone tunnel having a substantially constant cross-section over the length of the bone tunnel.

An additional object of the present invention is to provide a surgical bone reamer that avoids becoming impacted with bone when forming a bone tunnel.

Moreover, it is an object of the present invention to provide a surgical bone reamer for evacuating bone when forming a bone tunnel.

A further object of the present invention is to reduce exposure of a reaming head exteriorly of a bone surface when forming bone tunnels.

Some of the advantages of the surgical bone reamer of the present invention over the prior art are that bone smoke and heat related bone necrosis are eliminated when forming tunnels in bone, deposition of remnant bone on the walls of a bone tunnel is inhibited, drag on the reaming head when rotated in bone is reduced, efficiency of the reaming head when forming tunnels in bone is increased and the time required to form bone tunnels is reduced.

The surgical bone reamer according to the present invention is characterized by an elongated, rotatable shank having a proximal end, a distal end and a central longitudinal bore extending from the proximal end to the distal end. A reaming head is mounted on the distal end of the shank and includes a central longitudinal bore coaxially aligned with the bore in the shank and a plurality of equally spaced walls disposed radially around the central longitudinal axes of the bores. Tip surfaces are angularly joined to the radial walls to define drill tip edges disposed at an acute angle with a plane normal to the central longitudinal axis, such that tip edges disposed at 180° spaced locations around this axis define an included angle that facilitates penetration of the tip edges in bone when the reaming head is rotated. Reaming surfaces are angularly joined to the radial walls to define reaming edges extending longitudinally from the tip edges toward the proximal end parallel to and an equal radial distance from the central longitudinal axis for reaming a cylindrical tunnel when the reaming head is rotated in bone. Flutes are disposed between the tip surfaces and the radial walls and include bottom walls tapering inwardly from the tip surfaces to the radial walls and disposed at an angle with a plane normal to the central longitudinal axis to permit bone to be evacuated through the flutes when forming a tunnel in bone. Connecting surfaces join the reaming surfaces, the tip surfaces, and the bottom walls of the flutes to the radial walls along connecting edges disposed longitudinally on the radial walls parallel to the central longitudinal axis radially inwardly of the reaming edges to further promote evacuation of bone through the reaming head.

Other objects and advantages of the present invention will become apparent from the following description of the preferred embodiment taken in conjunction with the accompanying drawings wherein like parts in each of the several figures are identified by the same reference characters.

BRIEF DESCRIPTION OF THE DRAWINGS

FIG. 1 is a side view of the surgical bone reamer according to the present invention.

FIG. 2 is a front view of the surgical bone reamer of FIG. 1.

FIG. 3 is a rear view of the surgical bone reamer of FIG. 1.

FIG. 4 is a broken, perspective view of the surgical bone reamer of FIG. 1.

FIG. 5 is a sectional view taken along line 5—5 of FIG. 2.

DESCRIPTION OF THE PREFERRED EMBODIMENT

As shown in FIGS. 1-5, the surgical bone reamer 10 of the present invention includes an elongated, cylindrical shank or body 12 having a proximal end 14, a distal end 16 and a reaming head 18 mounted on the distal end 16. A central, longitudinal bore or cannulation 20 is formed in the shank 12 to extend longitudinally from the proximal end 14 to the distal end 16. Flats 22 are provided on the proximal end 14 at approximately 120° spaced locations, and the flats 22 extend longitudinally from the proximal end 14 toward the distal end 16. A circular aperture 24 is formed in the shank 12 to be positioned between a pair of the flats 22, and the aperture 24 extends through the shank 12 to communicate with the bore 20. The flats 22 permit the proximal end 14 to be inserted in an adaptor or chuck of a rotatable drive tool (not shown), and the aperture 24 allows the proximal end 14 to be retained in the adaptor by engagement of a ball detent on the adaptor in the aperture 24. Circumferential grooves 26 are formed exteriorly on the shank 12 at longitudinally spaced locations therealong calibrated to indicate the depth of the reaming head 18 in bone.

The reaming head 18 includes a base or end wall 28 having an annular recess 30 for securing therein the distal end 16 of the shank 12, and a central, longitudinal bore or cannulation 32 diametrically smaller than the bore 20 in coaxial alignment with the bore 20. Walls 34 are disposed around the bore 32 at approximately 90° spaced locations in radial alignment with the central longitudinal axis of the bore 32 or, in other words, the walls 34 are contained in planes intersecting the central longitudinal axis of the bore 32. A cutting or penetrating drill tip is defined on the walls 34 by angular drill tip edges 38 extending outwardly from the bore 32 in the direction of the base 28 angularly with the central longitudinal axis of the bore 32 as shown in FIGS. 1 and 4. Tip surfaces 40 are angularly joined to the radial walls 34 along the tip edges 38 at an acute angle A with a plane normal to the walls 34 along the tip edges 38 as shown in FIGS. 4 and 5. Reaming edges 42 on the radial walls 34 are joined to the tip edges 38 to extend longitudinally in the proximal direction parallel to and an equal radial distance from the central longitudinal axis of the bore 32 as shown in FIG. 1. Reaming surfaces 44 are angularly joined to the reaming edges 42 at an acute angle $A^1$ with a plane normal to the radial walls 34 along the reaming edges 42 as shown in FIG. 2, and the reaming surfaces 44 are joined to the tip surfaces 40. Reliefs 46 are joined to the reaming surfaces 44 to extend angularly downwardly therefrom to the base 28 as shown in FIGS. 1 and 4. The tip edges 38 define an acute angle with a plane normal to the central longitudinal axis of the bore 32 such that the tip edges 38 disposed at 180° spaced locations around the bore 32 define an obtuse included angle B in a plane containing the pair of tip edges as shown in FIG. 4. Flutes 48 are disposed between the tip surfaces 40 and the radial walls 34, and include a bottom wall 50 disposed at an acute angle C with a plane normal to the central longitudinal axis of the bore 32 as shown in FIG. 1. Planar connecting surfaces 52 disposed parallel with the longitudinal axis join the bottom walls 50, the reaming surfaces 44, the tip surfaces 40 and the radial walls 34, and the connecting surfaces 52 are joined to the radial walls 34 at connecting edges 54 extending longitudinally parallel to the central longitudinal axis of the bore 32 radially inwardly of the reaming edges 42. The connecting edges 54 extend longitudinally from a medial point on the radial walls 34 to the base 28, and the connecting surfaces 52 are angularly joined to the bottom walls 50 to meet the tip surfaces and the bottom walls at peaks 56 defined on and positioned medially on the the surfaces 40 such that the bottom walls 50 taper in a distal direction from the connecting surfaces 52 to the bore as shown in FIGS. 2 and 4. Curved notches are formed on the bottom walls 50 of the flutes 48 adjacent the bore 32 to define curved edges 58 extending from the tip surfaces 40 to the walls 34. The edges 58 define cusps 60 at the forwardmost end of the reaming head 18, and the cusps 60 define a C-shaped configuration in longitudinal section of the reaming head 18.

Preferably, the shank 12 and the reaming head 18 are formed of stainless steel. In one example, the outer diameter of the shank 12 is approximately 0.245 inches; the diameter of the bore 20 is approximately 0.119 inches; the diameter of the bore 32 is approximately 0.096 inches for insertion on an 0.095 inch diameter guide wire; the reaming edges 42 have a diameter in the range of approximately 0.354 inches to 0.472 inches; reliefs 46 define an angle of approximately 45° with the central longitudinal axis of the bore 32; the tip edges 38 define an angle of approximately 31° with a plane normal to the central longitudinal axis of the bore 32 such that the included angle B defined by the tip edges 38 disposed at 180° spaced locations is approximately 118°; the reaming surfaces 44 are joined to the radial walls 34 along the remming edges 42 at an angle $A^1$ of approximately 10°; the width of the reaming surfaces 44 measured between the radial walls 34 and the connecting surfaces 52 is approximately 0.025 inches; the tip surfaces 40 are joined to the radial walls 34 along the tip edges 38 at an angle A of approximately 10°; the bottom walls 50 of the flutes 48 define an angle of approximately 60° with a plane normal to the central longitudinal axis of the bore 32; the connecting edges 54 are positioned a constant radial distance of 0.148 inches from the central longitudinal axis of the bore 32; and the longitudinal length of the reaming head 18 measured from the base 28 to the cusps 60 is approximately 0.33 inches.

Numerous benefits are derived from the structural configuration and relative proportions discussed above. The cusps 60 and the included angle B defined by the drill tip edges 38 permit the reaming head 18 to easily penetrate and advance through bone when rotated by a drive tool without generating bone smoke and heat related bone necrosis. The reaming edges 42 parallel to the central longitudinal axis of the reaming head 18 produce a bone tunnel having a substantially constant cross-sectional configuration and insure straightness of the bone tunnel. The acute angles A and $A^1$ for the tip surfaces 40 and the reaming surfaces 44, respectively, enhance cutting effectiveness of the reaming head and allow bone fragments to be removed from the bone tunnel wall. The angled and tapered bottom walls 50 of the flutes 48 permit evacuation of bone through the flutes 48 during tunnel formation, and the radially inward position of the connecting edges 54 further promotes removal of bone fragments through the reaming head 18. The relatively shorter length of the reaming head 18 reduces the amount of time that the reaming head is exposed at the knee joint during formation of the femoral bone tunnel in endoscopic anterior cruciate ligament repair and replacement by allowing the reaming head to enter the femur in a relatively shorter period of time. The reliefs 46 reduce drag forces on the reaming head 18 when rotated in bone and, therefore, increase cutting efficiency and reduce cutting time in forming bone tunnels. The bore 20 being diametrically larger than the bore 32 ensures smooth insertion of the reamer 10 on a guide wire and compensates for inaccuracies in the guide bores.

In operation, the shank 12 is inserted in an adaptor or chuck of a rotatable drive tool, and the reamer 10 is inserted on a guide wire via the bores 20 and 32 through a remote portal, such as a portal leading to the tibia in endoscopic anterior cruciate ligament repair and reconstruction. The reaming head 18 is positioned adjacent a pre-selected site on the tibia and the drive tool is rotated. The cusps 60 initially penetrate the tibia, and the angular tip edges 38 easily enter and advance through the bone as the reaming head 18 is rotated The reaming edges 42 ream a longitudinally straight, open-ended bone tunnel in the tibia having a uniform, circular cross-section over the length of the bone tunnel. Bone fragments produced during formation of the bone tunnel are evacuated through the reaming head 18 via the flutes 48 and the connecting surfaces 52. The angularly disposed tip surfaces 40 and reaming surfaces 44 assist in removing bone fragments from the tunnel wall and enhance cutting effectiveness of the tip and reaming edges. The reliefs 46 promote forward advancement of the reaming head 18 through bone by reducing drag forces thereon during rotation. Once the tibial bone tunnel has been formed, the reamer 10 is passed intraarticularly across the knee joint to the femur, and is rotated by the drive tool to penetrate the femur at a pre-selected site. The rotating reaming head 18 remains exposed at the knee joint exteriorly of the femoral bone face for only a short period of time because the length of the reaming head is quickly accommodated in the femoral bone tunnel. Rotation of the reamer 10 is continued until a bone tunnel of the appropriate length is formed in the femur, as visually indicated by the grooves 26.

Inasmuch as the present invention is subject to many variations, modifications and changes in detail, it is intended that the subject matter discussed above and shown in the accompanying drawings be interpreted as illustrative and not in a limiting sense.

What is claimed is:

1. A surgical bone reamer comprising
   a rotatable body having a proximal end, a distal end, a longitudinal axis and a longitudinal bore extending from said distal end to said proximal end;
   a drill tip at said distal end including tip edges positioned around said axis and disposed angularly with a plane normal to said axis for penetrating bone;
   reaming edges joined to said tip edges and extending longitudinally from said tip edges to said proximal end parallel with said axis for forming a tunnel when said body is rotated in bone, said drill tip being tapered in a distal direction from said reaming edges to said bore;
   flute surfaces disposed between said tip edges for evacuating bone along said flute surfaces when said body is rotated in bone; and
   an elongate shank for mounting said body to rotate said body in bone.

2. A surgical bone reamer as recited in claim 1 wherein said flute surfaces are angularly disposed with said plane in the same direction as said tip edges.

3. A surgical bone reamer as recited in claim 2 wherein the angle defined by said flute surfaces with said plane is greater than the angle defined by said tip edges with said plane.

4. A surgical bone reamer as recited in claim 3 further including walls on said body positioned radially at equally spaced locations around said axis and wherein said tip edges and said reaming edges are defined on said walls.

5. A surgical bone reamer as recited in claim 4 further including tip surfaces on said body joined to said walls and reaming surfaces on said body joined to said walls and wherein said tip edges are defined where said tip surfaces are joined to said walls and said reaming edges are defined where said reaming surfaces are joined to said walls.

6. A surgical bone reamer as recited in claim 5 wherein said flute surfaces are angularly joined to said tip surfaces and said walls.

7. A surgical bone reamer as recited in claim 8 wherein said flute surfaces are tapered in a distal direction from said connecting surfaces to said distal end.

8. A surgical bone reamer as recited in claim 6 further including connecting surfaces joining said reaming surfaces, said walls, said tip surfaces and said flute surfaces.

9. A surgical bone reamer as recited in claim 7 wherein said connecting surfaces are joined to said walls along connecting edges extending longitudinally along said walls parallel with said axis and radially inwardly of said reaming edges.

10. A surgical bone reamer as recited in claim 9 wherein said connecting edges extend longitudinally along said walls toward said proximal end from locations on said walls medially disposed between said distal and proximal ends.

11. A surgical bone reamer as recited in claim 10 wherein said connecting surfaces are angularly joined to said flute surfaces and said tip surfaces at peaks defined on said tip surfaces.

12. A surgical bone reamer as recited in claim 11 wherein said tip edges are positioned at approximately 90° spaced locations around said axis.

13. A surgical bone reamer as recited in claim 12 wherein said tip edges define an angle of substantially 31° with said plane.

14. A surgical bone reamer as recited in claim 13 wherein said flute surfaces are define an angle of substantially 60° with said plane.

15. A surgical bone reamer as recited in claim 8 wherein said comprising
a rotatable body having a proximal end, a distal end and a longitudinal axis;
walls on said body positioned radially at equally spaced locations around said axis and having tip edges acutely angled toward said proximal end in a direction outwardly from said axis for penetrating bone and reaming edges extending longitudinally, proximally from said tip edges for reaming a cylindrical tunnel when said body is rotated in bone;
tip surfaces are angularly joined to said walls along said tip edges, said
reaming surfaces are angularly joined to said walls along said reaming edges and said 16. A surgical bone reamer as recited in claim 15 wherein said tip surfaces are joined to said walls at an acute angle with a plane normal to said walls along said tip edges.

17. A surgical bone reamer as recited in claim 16 wherein said reaming surfaces are joined to said walls at an acute angle with a plane normal to said walls along said reaming edges.

18. A surgical bone reamer as recited in claim 17 wherein said acute angle for said tip surfaces is approximately 10°.

19. A surgical bone reamer as recited in claim 18 wherein said acute angle for said reaming surfaces is approximately 10°.

20. A surgical bone reamer as recited in claim 19 wherein said walls include four walls positioned at approximately 90° spaced locations around said axis.

21. A surgical bone reamer as recited in claim 20 wherein said tip edges for a pair of walls positioned at approximately 180° spaced locations around said axis define an included angle of substantially 118° in a plane containing said pair of walls.

22. A surgical bone reamer comprising
a rotatable body having a proximal end, a distal end, a central longitudinal bore extending from said proximal end to said distal end and a longitudinal axis;
walls on said body positioned around said bore in planes radially aligned with said axis;
reaming edges on said walls extending longitudinally from said proximal end toward said distal end, said reaming edges being disposed an equal radial distance from said axis for forming a cylindrical tunnel when said body is rotated in bone;
tip surfaces joined to said walls and defining, walls, tip edges disposed in said planes of said walls, said tip edges extending angularly, distally from said reaming edges to said bore at said distal end;
notches disposed between said walls at said distal end and including curved edges extending proximally from said distal end to said walls for defining cusps at said distal end for initially entering bone when said body is rotated therein; and
a shank mounting said body to rotate said body in bone.

23. A surgical bone reamer as recited in claim 22 wherein said body includes an end wall at said proximal end having a recess receiving an end of said shank.

24. A surgical bone reamer as recited in claim 23 further including a bore in said shank axially aligned with said bore in said body.

25. A surgical bone reamer as recited in claim 24 further including relief surfaces angularly joining said reaming edges and said end wall.

26. A surgical bone reamer as recited in claim 25 wherein said shank bore is diametrically larger than said body bore.

27. A surgical bone reamer as recited in claim 26 wherein said relief surfaces define an angle of approximately 45° with said longitudinal axis.

28. A surgical bone reamer as reciter in claim 27 wherein the length of said body from said end wall to said distal end is approximately 0.33 inches.

29. A surgical bone reamer as recited in claim 28 further including a plurality of flats extending longitudinally along said shank for engaging a rotatable drive tool.

30. A surgical bone reamer as recited in claim 29 further including an aperture positioned between said flats to receive a detent on the drive tool for securing said shank to the drive tool.

31. A surgical bone reamer as recited in claim 30 further including means on said shank for indicating the depth of said body in bone.

32. A surgical bone reamer as recited in claim 31 wherein said indicating means includes a plurality of circumferential grooves on said shank at longitudinally spaced locations therealong.

* * * * *

UNITED STATES PATENT AND TRADEMARK OFFICE
CERTIFICATE OF CORRECTION

PATENT NO.   : 5,190,548
DATED        : March 2, 1993
INVENTOR(S)  : Robert Davis It is certified that error appears in the above-identified patent and that said Letters Patent is hereby corrected as shown below:

Column 5, line 12, delete "remming" and insert --reaming--.
    Column 7, line 28, delete "are".
    Column 7, line 31, delete "comprising".
    Column 7, lines 32 - 34, delete in their entireties.
    Column 7, line 35, delete "spaced locations around said axis and having".
    Column 7, line 36, after "edges", insert --are--.
    Column 7, line 38, delete "and" and insert --, said--.
    Column 7, line 38, delete "extending" and insert --extend--.
    Column 7, line 40, delete ";" and insert --, said--.
    Column 7, line 44, after "said", insert --connecting surfaces are planar--.

Signed and Sealed this

Twelfth Day of April, 1994

Attest:

BRUCE LEHMAN

Attesting Officer

Commissioner of Patents and Trademarks